(12) United States Patent
Duff et al.

(10) Patent No.: US 11,554,233 B2
(45) Date of Patent: Jan. 17, 2023

(54) POWERED APPARATUS FOR A PERSONAL PROTECTION RESPIRATORY DEVICE

(71) Applicant: 3M INNOVATIVE PROPERTIES COMPANY, St. Paul, MN (US)

(72) Inventors: John A. Duff, London (GB); Benjamin H. Cooper, Auckland Park (GB); Jason A. Graves, Cleatlam (GB); Henning T. Urban, Durham (GB)

(73) Assignee: 3M Innovative Properties Company, St. Paul, MN (US)

( * ) Notice: Subject to any disclaimer, the term of this patent is extended or adjusted under 35 U.S.C. 154(b) by 553 days.

(21) Appl. No.: 16/476,327

(22) PCT Filed: Jan. 11, 2018

(86) PCT No.: PCT/US2018/013340
§ 371 (c)(1),
(2) Date: Jul. 8, 2019

(87) PCT Pub. No.: WO2018/132587
PCT Pub. Date: Jul. 19, 2018

(65) Prior Publication Data
US 2020/0038614 A1     Feb. 6, 2020

(30) Foreign Application Priority Data
Jan. 12, 2017  (GB) ..................................... 1700576

(51) Int. Cl.
*A61M 16/06*     (2006.01)
*A61M 16/00*     (2006.01)
*A61M 16/10*     (2006.01)

(52) U.S. Cl.
CPC .... *A61M 16/0616* (2014.02); *A61M 16/0009* (2014.02); *A61M 16/0069* (2014.02);
(Continued)

(58) Field of Classification Search
CPC .......... A61M 16/0616; A61M 16/0069; A61M 16/06; A61M 16/022; A61M 16/0057;
(Continued)

(56) References Cited

U.S. PATENT DOCUMENTS 4,549,452 A * 10/1985 Jobst .................... B26D 7/1863
                                                                83/100
4,549,542 A    10/1985 Chien
(Continued)

FOREIGN PATENT DOCUMENTS

| CN | 202236942 | 5/2012 |
| CN | 204655706 | 9/2015 |

(Continued)

OTHER PUBLICATIONS

International Search report for PCT International Application No. PCT/US2018/013340 dated Apr. 24, 2018, 5 pages.

*Primary Examiner* — Kendra D Carter
*Assistant Examiner* — Thomas W Greig
(74) *Attorney, Agent, or Firm* — Steven A. Bern

(57) ABSTRACT

There is provided an exhaust apparatus for connection to a personal protection respiratory device that defines a filtered air volume adjacent to the face of a wearer and comprises at least one exhalation, the apparatus comprising a blower in fluid connection with the at least one exhalation valve, the blower being responsive to the wearer's respiratory cycle to draw a substantial portion of the wearer's exhaled breath through the at least one exhalation valve wherein, in response to the wearer's respiratory cycle, the blower operates throughout the wearer's exhale breath, or a substantial period thereof, and does not operate throughout the wearer's inhale breath, or a substantial period thereof.

19 Claims, 15 Drawing Sheets

(52) U.S. Cl.
CPC ...... *A61M 16/022* (2017.08); *A61M 16/0683* (2013.01); *A61M 16/107* (2014.02); *A61M 16/1065* (2014.02); *A61M 2205/8206* (2013.01)

(58) Field of Classification Search
CPC ............ A61M 16/0066; A61M 16/107; A62B 18/006; A62B 18/00; A62B 18/0045; A62B 17/00; A62B 18/02; A62B 18/025; A62B 18/04; A62B 18/045
See application file for complete search history.

(56) References Cited

U.S. PATENT DOCUMENTS

| | | | |
|---|---|---|---|
| 4,646,732 A | 3/1987 | Chien | |
| 5,372,130 A * | 12/1994 | Stern | A62B 18/006 128/206.17 |
| 8,584,676 B2 * | 11/2013 | Gossweiler | A62B 18/006 128/206.16 |
| 9,901,758 B2 * | 2/2018 | Furuichi | A62B 18/08 |
| 10,512,749 B2 * | 12/2019 | Lurie | A61M 16/208 |
| 2006/0076012 A1 * | 4/2006 | Tanizawa | A62B 18/006 128/206.16 |
| 2010/0313892 A1 * | 12/2010 | Shigematsu | A62B 18/10 128/207.12 |
| 2012/0222674 A1 * | 9/2012 | Ono | A62B 9/006 128/202.22 |
| 2014/0261425 A1 * | 9/2014 | Connor | A61M 16/06 128/204.23 |

FOREIGN PATENT DOCUMENTS

| | | |
|---|---|---|
| TW | 200507900 | 3/2005 |
| WO | WO 2014-081788 | 5/2014 |
| WO | WO 2017-007633 | 1/2017 |

* cited by examiner

POWERED APPARATUS FOR A PERSONAL PROTECTION RESPIRATORY DEVICE

CROSS REFERENCE TO RELATED APPLICATIONS

This application is a national stage filing under 35 U.S.C. 371 of PCT/US2018/013340 filed Jan. 11, 2018, which claims the benefit of Great Britain Application No. 1700576.0, filed Jan. 12, 2017, the disclosure of which is incorporated by reference in its/their entirety herein.

TECHNICAL FIELD

The present disclosure relates to an exhaust apparatus for personal protection respiratory devices, particularly, but not exclusively to negative pressure respirators. In particular, the present disclosure relates to a powered apparatus which can be connected, either permanently or releasably, to a personal protection respiratory device. In use, the powered apparatus reduces inhalation effort and removes the hot and moist air that can often build-up inside a negative pressure respirator to significantly improve and enhance wearer comfort, whilst maximizing filter life and minimizing respiratory effort.

BACKGROUND

Negative pressure respirators are well known in the art. With respirators of this type, filtered air is drawn into the enclosed space between the inside of the respirator and a wearer's face through a filter system by the wearer's breathing action. When the wearer draws a breath, negative pressure is created in the respirator and air is drawn in through the filter system. When the wearer exhales a breath, spent air leaves the respirator through an exhalation valve and/or back through the filter system.

Although negative pressure respirators are available in many different configurations, and offer many different benefits, they all have one major drawback, that of the uncomfortable build-up of heat and moisture that can sometimes occur inside the respirator. The heat and moisture build-up is caused by the trapping of the wearer's exhaled breath in the cavity created between the respirator and the wearer's face. As the wearer works harder, and/or wears the respirator for extended periods of time, heat and moisture build-up may increase.

Many different solutions have been proposed in the prior art to eliminate, or at least minimise, the problem of heat and moisture build-up inside negative pressure respirators. For example, the addition of exhalation valves, and optimising the operation of these exhalation valves. The design and optimisation of low pressure drop filters and media has also been proposed to alleviate this problem and/or by controlling the filter surface area and filter material pressure drop. Another solution in the prior art is to include pads to absorb the moisture.

A further solution is offered in WO2014/081788 in which a respirator has a blower in fluid connection with the exhalation valve, the blower being operable to draw the wearer's exhaled breath through the valve. This solution presents advantages but also has drawbacks in that the blower applies a constant negative pressure to the exhale valve. This can lead to increased inhalation effort and decreased filter life as a result of the increased flow of air passing through the filter.

A known improvement to the device of WO2014/081788 is to control the blower so that the blower so that the blower preferably only operates during the exhale breath. This has the advantage that the user no longer needs to overcome the blower during the inhale stroke. Whilst this reduces the inhalatory effort over known devices, the user must still overcome the pressure drop delivered by the filter medium. This can be significant dependent on the type of filter in use and the extent of the respiratory effort of the user.

It is therefore an object of the disclosure to deliver the improved cooling effects of the prior art device whilst reducing the inhalation effort required to overcome the filter pressure drop.

Accordingly, a first aspect of the present disclosure provides an exhaust apparatus for connection to a personal protection respiratory device that defines a filtered air volume adjacent to the face of a wearer and comprises at least one exhalation valve and at least one inhalation valve, the apparatus comprising:

a first air duct in fluid connection with the at least one exhalation valve, a second air duct in fluid connection with the at least one inhalation valve, a blower assembly for selectively directing air through the first and second ducts the blower assembly being responsive to the wearer's respiratory cycle so that, in use, the blower draws a substantial portion of the wearer's exhaled breath through the first duct and out through the at least one exhalation valve, and the blower draws a substantial portion of the wearer's inhaled breath through the second duct and in through the at least one inhalation valve.

Operating the blower selectively to draw air through the exhalation valve during user exhalation or draw air through the inhalation valve during user inhalation (or a substantial part thereof) delivers significant advantages to the present disclosure as follows.

Firstly, the inhalation effort of the user is reduced since the pressure drop generated by the filter is at least in part, but potentially entirely, compensated by the blower. In the prior art device the user must generate sufficient back pressure to overcome the filter pressure drop before any air flow passes through the filter. This additional pressure must be maintained throughout the inhalation in order for the user to draw sufficient air into the lung cavity to meet physiological demand. This is not the case in the present disclosure where the blower overcomes the pressure enabling the user to breath "normally", that is to say breath as if the filter was not present in the air flow path to the lungs. This is a significant advantage where heavy duty filters with a significant pressure drop are required.

Secondly, it is possible to operate the blower so as to achieve a positive pressure in the filtered air volume when averaged over the respiratory cycle. This reduces the risk of the filtered air volume becoming compromised by leakage of ambient air between the filter and the user's face during use. This increases the efficacy of the respiratory device.

Preferably, the blower assembly comprises a first blower associated with the first air duct, and a second blower associated with the second air duct, the first and second blowers being responsive to the wearer's respiratory cycle, wherein the first blower operates throughout the wearer's exhale breath, or a substantial period thereof, and does not operate throughout the wearer's inhale breath, or a substantial period thereof, and the second blower operates throughout the wearer's inhale breath, or a substantial period thereof, and does not operate throughout the wearer's exhale breath, or a substantial period thereof.

Preferably, the exhaust apparatus further comprises
a controller,
a sensor for sensing a parameter generated by the wearer's breathing cycle and sending a signal indicative of the parameter to the controller,
the controller being in communication with the sensor and the first and second blower,
wherein the controller operates the first and second blower in response to the signal.

Preferably, the parameter is pressure, the sensor is a pressure sensor and the signal is a pressure signal.

Preferably, the pressure is sensed in a filtered air volume of the personal protection respiratory device.

Alternatively, the pressure is sensed downstream of the exhalation valve or upstream of the inhalation valve.

Preferably, the controller stops the first and starts the second blower when the pressure sensed by the pressure sensor falls below a second predetermined pressure or the rate of change of pressure reaches a second predetermined rate.

Preferably, the controller stops the first and starts the second blower when the pressure sensed by the pressure sensor falls below a second predetermined pressure or the rate of change of pressure reaches a second predetermined rate.

Preferably, the first predetermined pressure and the second predetermined pressure are a common predetermined pressure.

Preferably, the common predetermined pressure is substantially ambient pressure so that the controller starts the first blower and stops the second blower substantially at the initiation of the wearer's exhale breath and stops the first blower and starts the second blower substantially at the end of the wearer's exhale breath.

Alternatively, the common predetermined pressure is higher than ambient pressure so that the controller starts the first blower and stops the second blower momentarily after the initiation of the wearer's exhale breath and stops the first blower and starts the second blower momentarily before the end of the wearer's exhale breath.

Alternatively, the common predetermined pressure is lower than ambient pressure so that the controller starts the first blower and stops the second blower momentarily before the initiation of the wearer's exhale breath and stops the first blower and starts the second blower momentarily after the end of the wearer's exhale breath.

Alternatively, the first predetermined pressure is greater than the second predetermined pressure so that the controller starts the first blower and stops the second blower momentarily after the initiation of the wearer's exhale breath and stops the first blower and starts the second blower momentarily after the end of the wearer's exhale breath.

Preferably, the second predetermined pressure is greater than the first predetermined pressure so that the controller starts the first blower and stops the second blower momentarily before the initiation of the wearer's exhale breath and stops the first blower and starts the second blower momentarily before the end of the wearer's exhale breath.

Preferably, the first and second blowers further comprise an inlet, a motor, a fan, and an outlet.

Preferably, the personal protection respiratory device is selected from a group consisting of disposable, reusable, half mask, full face, particulate, gas and vapour and tight-fitting hood respirators.

BRIEF DESCRIPTION OF THE FIGURES

The present disclosure will now be described by way of example only, and with reference to the accompanying drawings, in which.

DETAILED DESCRIPTION

Figure 1:
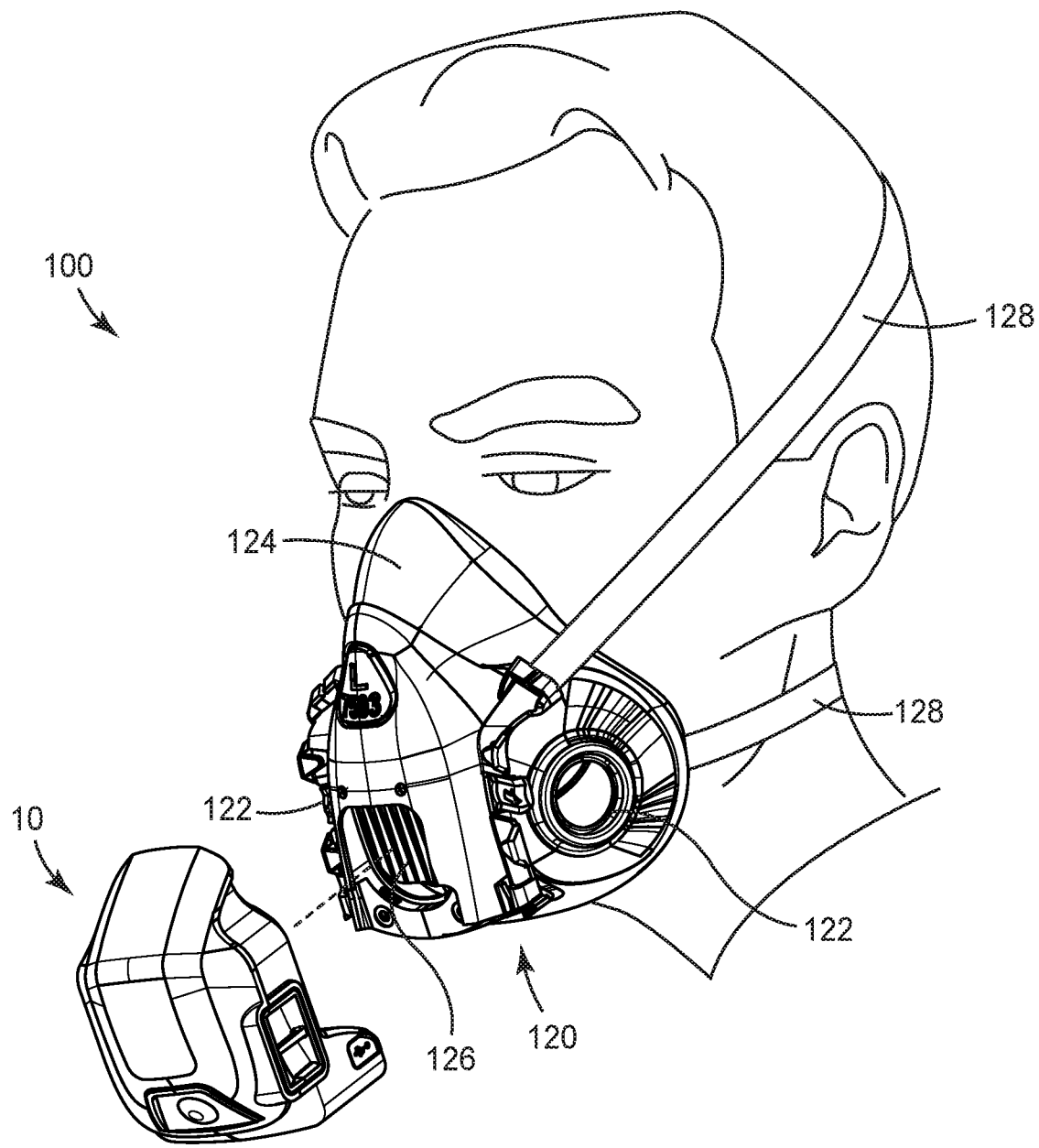
FIG. 1 is an exploded front side perspective view of a known exhaust apparatus for connection to a personal protection respiratory device.

FIG. 1 is an exploded view of a known exhaust apparatus indicated generally at 10. The apparatus 10 is able to connect or otherwise engage to or with a personal protection respiratory device 120, also known as a respirator, either in a permanent fashion or in a releasable manner as will be described in further detail shortly.

Whilst the respirator 120 illustrated in FIGS. 1, 2, 5, and 7 is indicative of the 3M™ 7500 Series of gas, vapour and particulate respirators, the exhaust apparatus 10 can be utilised with any negative pressure respiratory device 120. The skilled person will appreciate that the term "respirator" or "respiratory mask", as used interchangeably herein, is intended to mean a breathing device worn to prevent the inhalation of hazardous substances, particles, vapours or noxious gases. The term "negative pressure respiratory mask" is intended to cover any respirator in which the air pressure inside the mask becomes lower than the ambient air pressure when the wearer inhales.

A negative pressure respiratory mask 120 as described herein is used to mean any form of respirator intended to fit the face of the wearer 100 in a substantially sealed configuration causing the air inhaled and exhaled by the wearer 100 to pass through a filter body or a filter portion of the respirator or exhalation valve). Negative pressure respiratory mask 120 can be full or half facepiece mask, depending upon the hazard of concern. Again, these masks utilise a filter which prevents the inhalation of contaminants, particles, gases and vapours from the air inhaled by the wearer. Some common examples of this type of respirator are manufactured by 3M Company located in St. Paul, Minn., and include the 3M™ 4000, 6000 and 6500 Series of reusable respirators or tight-fitting hood facepiece respirators.

Disposable respirators, such as the 3M™ 8000 and 9000 Series of cup-shaped and flat-folded products, are lightweight single-piece respirators that employ a filter media which removes particulates and mists from the air stream as the wearer draws a breath. The entire unit is designed to be discarded after some extended period or a single use or single shift, depending on the contaminant. Filtering facepieces, such as the 3M™ 4000, 6000 and 6500 Series are generally reusable products and which can have replaceable filter cartridges. Typically one or two cartridges attach securely to half mask or full facepiece which has built into it a corresponding number of valves for inhalation, and usually one for exhalation.

The personal protection respiratory device 20 that is illustrated in FIG. 1 is a 3M™ 7500 half mask to which filters can be attached using bayonet connectors.

Figure 2:
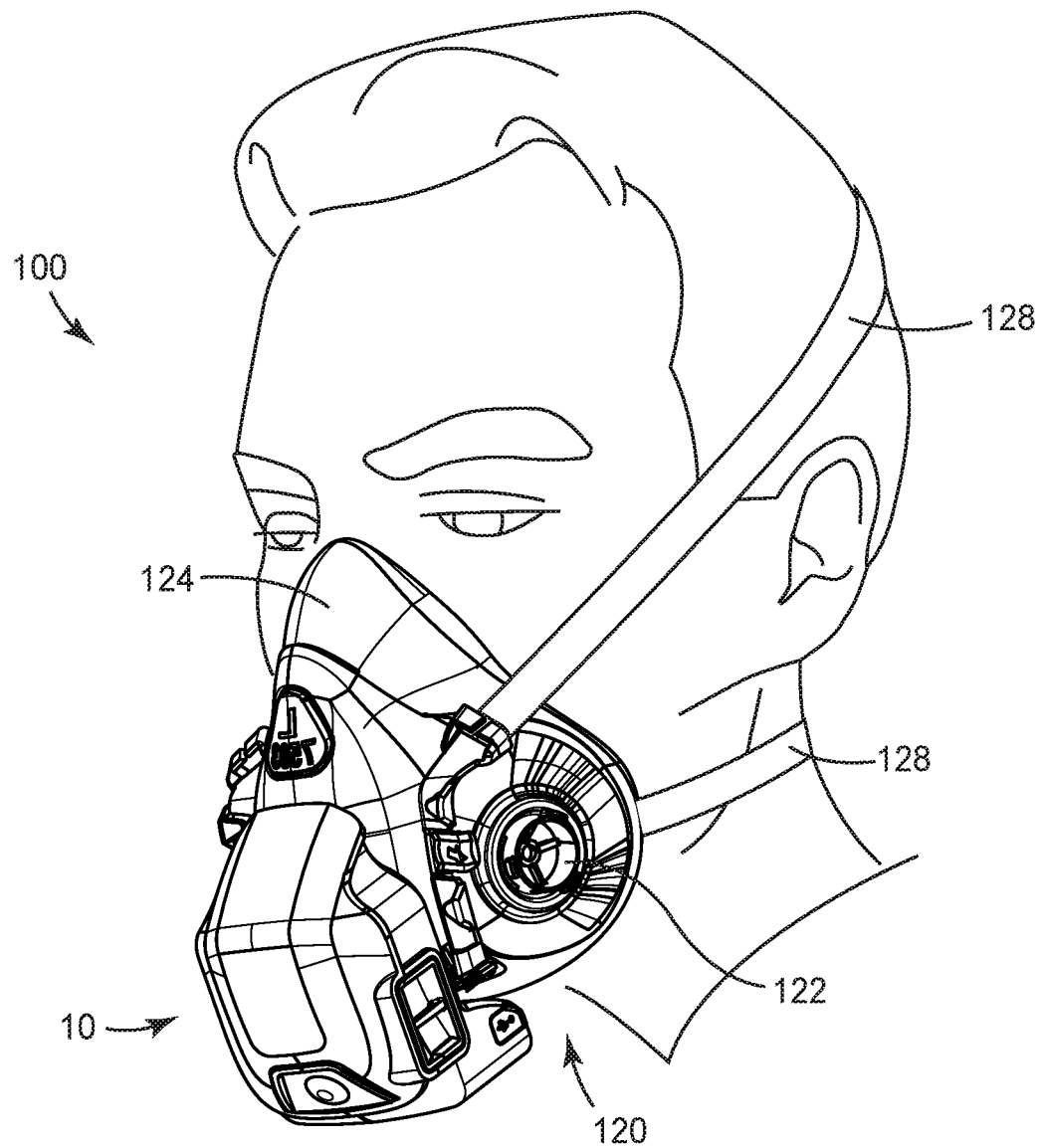
FIG. 2 is a front side perspective view of the exhaust apparatus of FIG. 1 connected to the personal protection respiratory device 2.

Referring to FIGS. 1 and 2, a pair of filter cartridges (not shown for clarity) are attached to the respirator mask 120 at respective inhalation ports 122. Each of the inhalation ports 122 has a respective inhalation valve 136 (shown in FIG. 7) on the inside of the respirator mask 120 which open as a wearer 100 draws a breath. The face mask 120 has an exhalation valve 126 with a one-way exhalation valve diaphragm 138 (shown in FIG. 7) which open as a wearer 100 expels a breath. The mask 120 is held in position on the wearer's head by adjustable straps 128 (shown only in FIGS. 1 and 2).

The respiratory mask 120 has a conformable gasket or seal 124 which generally encloses the wearer's 100 mouth and nose. Since a good seal is needed to ensure filtration of the containments, one drawback in the prior art is that sometimes an uncomfortable build-up of heat and moisture is noticed by the wearer 100 inside the respirator 120. As the wearer 100 works harder, and or wears the respirator 120 for extended periods of time, heat and moisture build-up can occur. The heat and moisture build-up is caused by the trapping of the exhaled breath in the cavity created between the respirator 120 and the wearer's 100 face.

Figure 3:
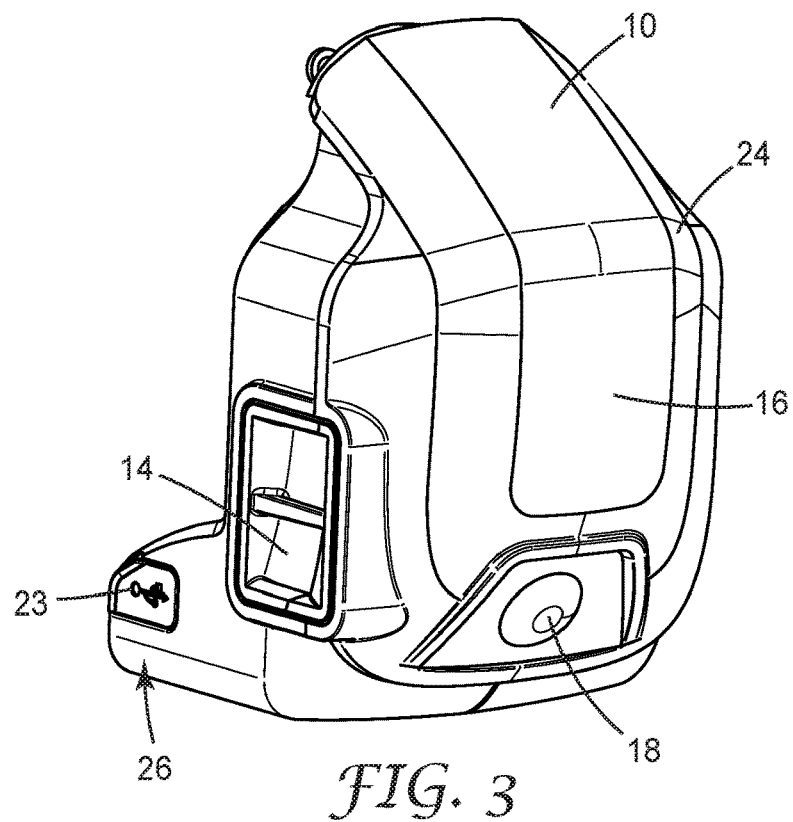
FIG. 3 is a front side perspective view of the exhaust apparatus of FIG. 1.
Figure 4:
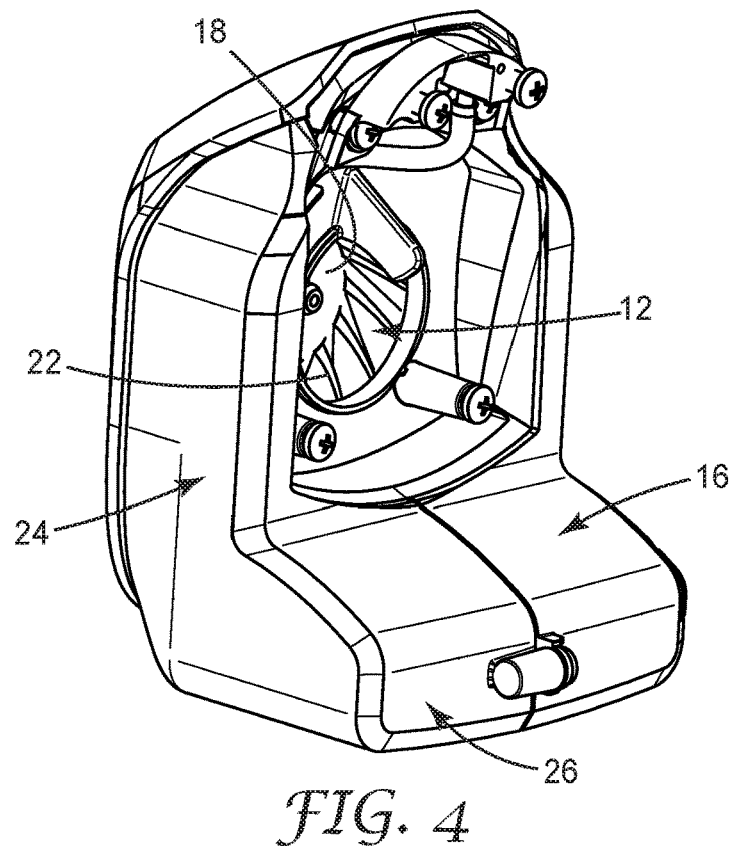
FIG. 4 is a rear side perspective view of an exhaust apparatus of FIG. 1.

As illustrated in FIGS. 1 and 2, and in further detail in FIGS. 3 and 4, an exhaust apparatus 10 is shown having a housing 16 with a generally L-shaped form. The exhaust apparatus 10 includes an inlet 12 (see FIG. 4) and an outlet 14 (see FIG. 3). The outlet 14 is formed in a side surface of the housing 16. Positioned inside housing 16 between the inlet 12 and the outlet 14 is a blower 18 which in use draws air out of the respiratory device 120. The blower 18 has a motor 20 which drives a fan 22. The motor 20 is powered by a battery 25, which will be described in further detail shortly with reference to FIG. 6.

The apparatus 10 has a housing 11 defined by upwardly extending section indicated generally at 24 which houses the inlet 12, outlet 14 and blower 18. The housing 11 also has a rearwardly extending section indicated generally at 26 which houses the battery 25 and a controller 28 (shown in FIG. 6). The positioning of the battery 25 (a relatively heavy component of the device 10) in the rearwardly extending section 26 allows the centre of mass of the device to sit most closely to the centre of mass of the head. This improves the comfort of the apparatus by minimizing the moment of inertia of the device as the user 100 moves his or her head during use.

To operate the apparatus, a switch mechanism 18 is accessible to the wearer 100. The switch mechanism 18 can have a simple on/off mode of operation or can include a variable adjustment so that the wearer 100 can optimise the desired blower speed, and hence, cooling effect based upon the environmental conditions, the task the wearer 100 is undertaking, and the wearer's personal choice. Alternatively the settings may be preconfigured by connection to managing software on a PC via USB connection port 23. The connection port 23 also serves as a charging port for the battery 25.

In use a cooling effect is achieved by the exhaust apparatus 10 as follows. When the wearer 100 inhales a breath, "cooler" ambient air is drawn into the respiratory mask 20 either though the filter cartridges and inlet ports 122 as shown in FIGS. 1 and 2 in the case of a reusable mask, or through, for example, a filter portion or filtering mask body of the respirator, in the case of a disposable mask. Heat and moisture build-up is then caused by trapping the exhaled breath in the cavity created between the respirator 120 and the wearer's 100 face. When operated, the exhaust apparatus 10 draws this warm and moist air out through the exhaust valve 126 during the exhale breath and reduces the exhalation breathing resistance, as described below. This produces a noticeable cooling benefit for the wearer 100 without placing a respiratory burden on the inhale breath or reducing the life of the filter.

Figure 5:
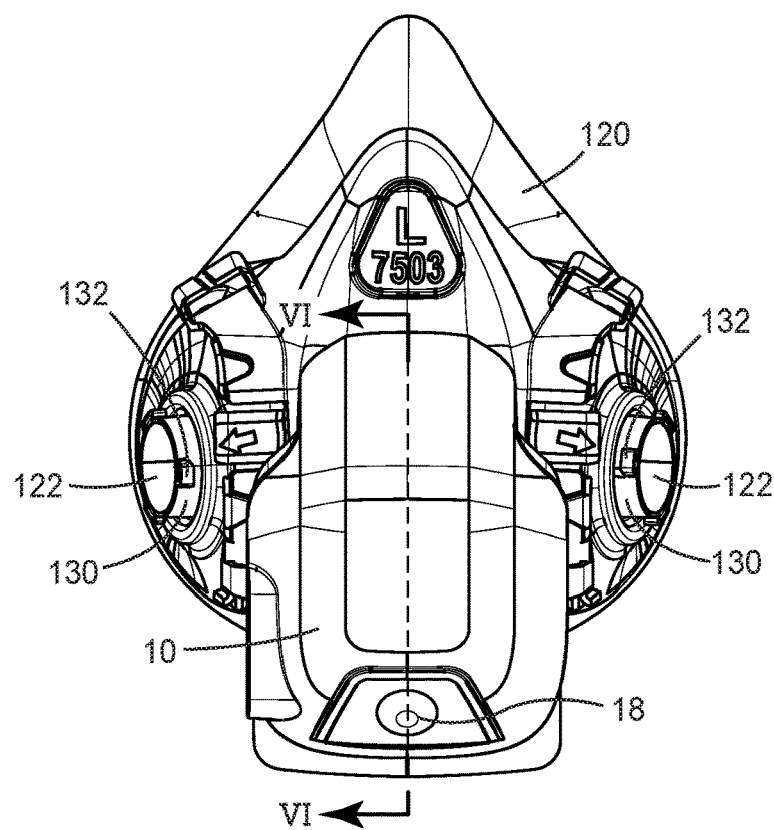
FIG. 5 is a front view of the exhaust apparatus of FIG. 1 connected to the personal protection respiratory device of FIG. 1.

Turning now to FIG. 5, the exhaust apparatus 10 is shown connected to the respirator 120. The mechanism for connection will be described in further detail below. FIG. 5 shows in greater detail the inlet ports 122 which are defined by port walls 130 which have bayonet fitting 132 of known design. The bayonet fittings 132 are provided to connect to the 3M™ 2000, 5000 or 6000 series of filters. However, it will be appreciated that alternative attachments mechanisms such as the DIN threaded filters may be provided in order to accept differing types of filters. Furthermore, an integral cartridge may be provided in line with the 3M™ 4000 series half masks.

The inlet 12 of the exhaust device 10 is shaped to releasably connect by way of an interference fit to the shape and dimensions of the respective exhaust valve 126 situated on the respiratory mask 120. Whilst the exhaust apparatus 10 described herein in relation to FIG. 5 connects by way of an interference fit, the skilled person will appreciate that any form of releasable connection to the exhaust valve 126 is possible, including, for example, connection by way of a screw thread, snap fit engagement, bayonet, quick release mechanism etc. The above list is in no way intended to be limiting and exhaustive.

As an alternative to releasable connection described above, it may be desirable to utilize a direct permanent connection between the device 10 and the respiratory mask 120. Such connection might be by welding, adhesive or other known attachment mechanism such as attachment by screw as will be described in further detail shortly.

Figure 6:
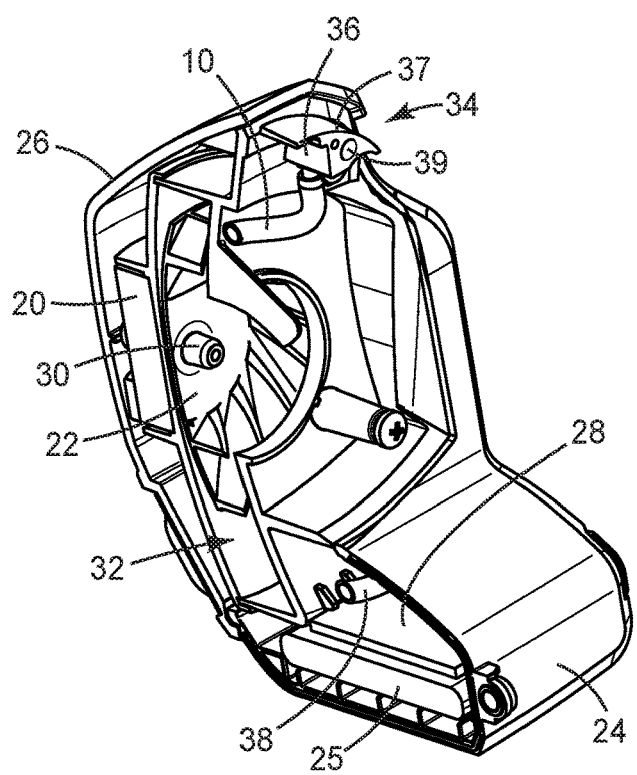
FIG. 6 is a cross-sectional rear side view of the exhaust apparatus of FIG. 1 taken along the dashed line VI-VI in FIG. 5.
Figure 7:
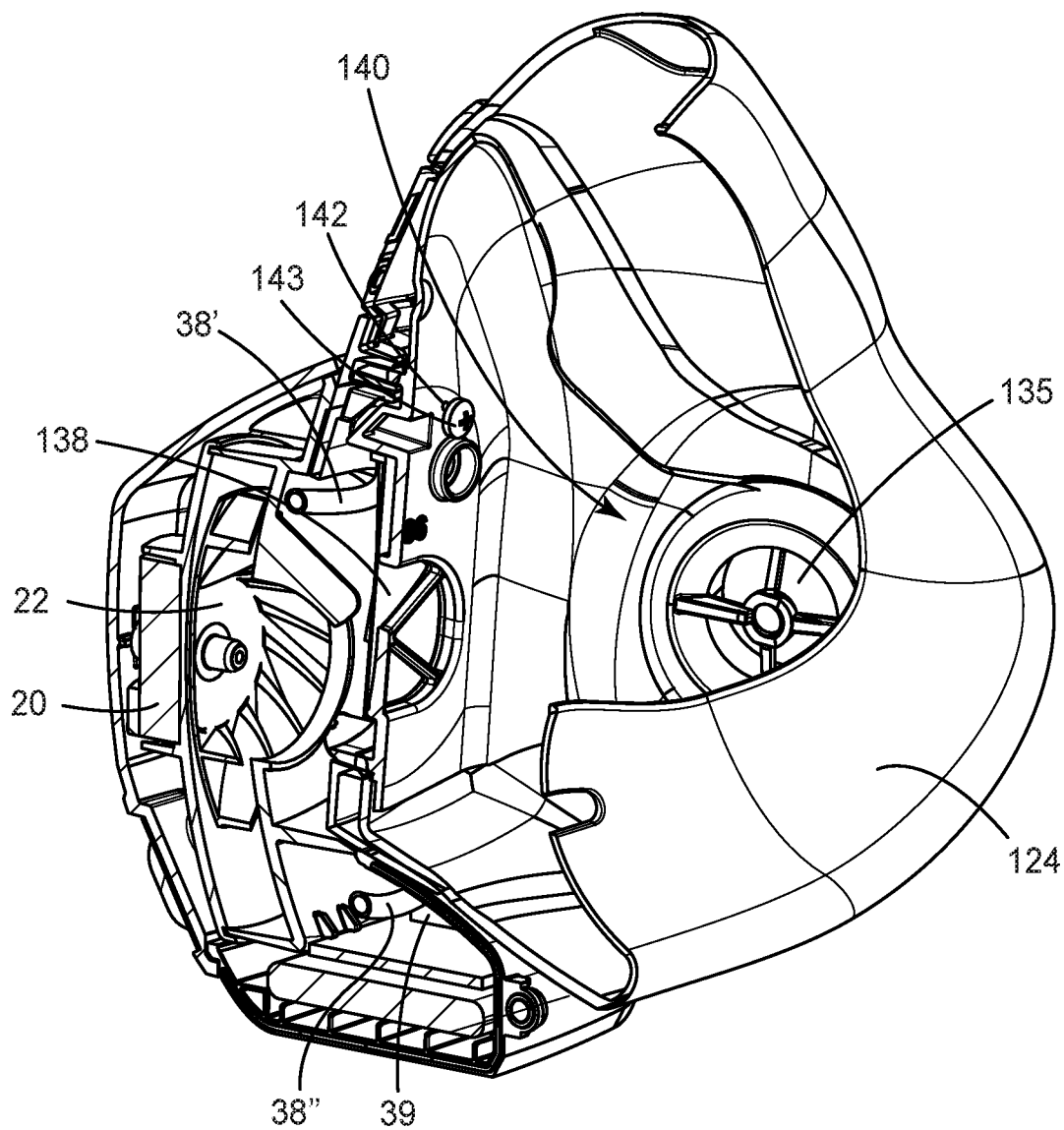
FIG. 7 is a cross-sectional rear side view of the exhaust apparatus of FIG. 1 connected to the personal protection respiratory device of FIG. 1 taken along the dashed line VI-VI in FIG. 5.

Referring now to FIGS. 6 and 7 the motor 20 is shown mounted within the upwardly extending section 26 of the exhaust apparatus 10. The motor 20 drives a shaft 30 which in turn drives the fan 22. When operative, the fan 22 draws air from the filtered air cavity (indicated generally at 140 in FIG. 7) of the respirator 120 past the valve 138 and expels the air through the fan scroll 32 which is connected to the outlet 14. In this way operation of the motor 20 is able to draw air from the cavity 140 and expel it to atmosphere. The motor 20 is powered by the battery 25 which is situated in the rearwardly extending section 26. Directly above the battery 25 is a controller 25 in the form of a microprocessor on PCB. The controller 28 is programmed to control the motor 20 is response to the wearer's breathing cycle.

The wearer's breathing cycle is detected by measuring the pressure of the filtered air volume in the filtered air cavity 140. This is achieved via a pressure port 142 (see FIG. 7) in the respirator 120. The pressure port 142 is in fluid communication with a pressure conduit 34 in the device 10. The pressure conduit is defined by a connector 36 and a pipe 38, the two ends of which 38', 38" are shown in FIG. 6. The connector 36 has an orifice 37 in fluid communication with the pressure port 142. The connector 36 seals against the forward face of the respirator 120 under the action of screw 143 (a second corresponding screw on the opposite side of the device 120 is not shown for clarity and by virtue of the cross-sectional view of FIG. 7) which passes through a hole 39 in the connector 36. The screw 143 also acts to supplement the interference fit between the exhaust apparatus 10 and the respirator 120 to mechanically attach the apparatus 10 to the device 120. The second end 38" of the pipe 38 is connected to a pressure transducer 39 (shown only in FIG. 7) which detects the pressure and sends a signal to the controller 28. It is conceivable within the scope of the application that the pressure generated by the wearer's breath could be measured at a position other than in the filtered air volume. For example the pressure could be detected downstream of the exhalation valve. This would remove the necessity for the connector 36 and pressure port 142 and their sealed interface. Alternatively the pressure could be sensed upstream of the inhalation valve at the inhalation ports 122.

Figure 8:
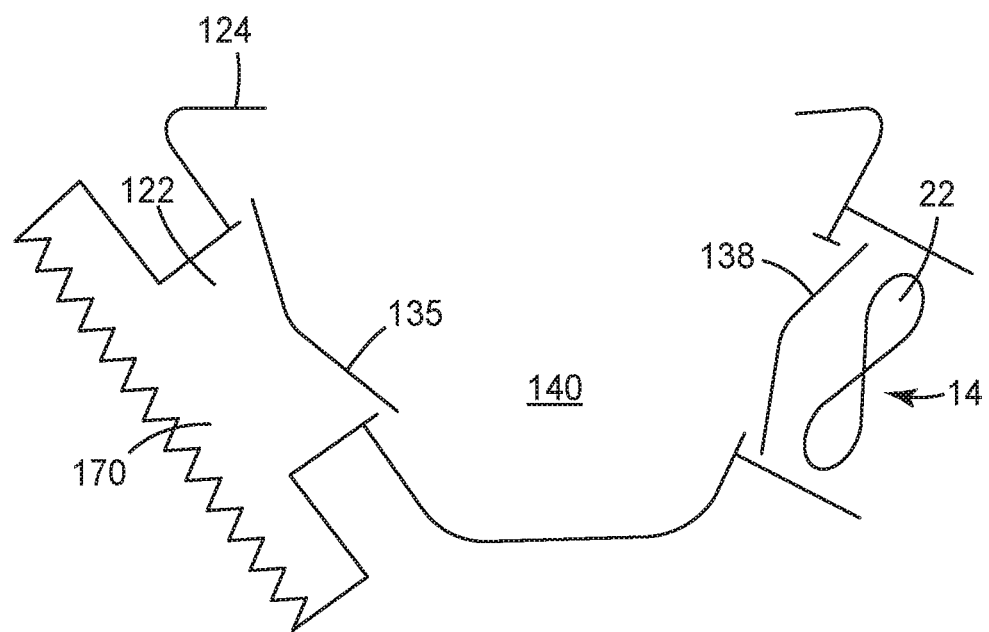
FIG. 8 is a schematic representation of the exhaust apparatus of FIG. 1 connected to a personal protection respiratory device.

Turning now to FIG. 8, the exhaust apparatus 10 and respirator 120 are shown schematically. The fan 22 is shown in a different position to in FIGS. 1 to 7 and a single filter cartridge 170 is shown for clarity.

Figure 9:
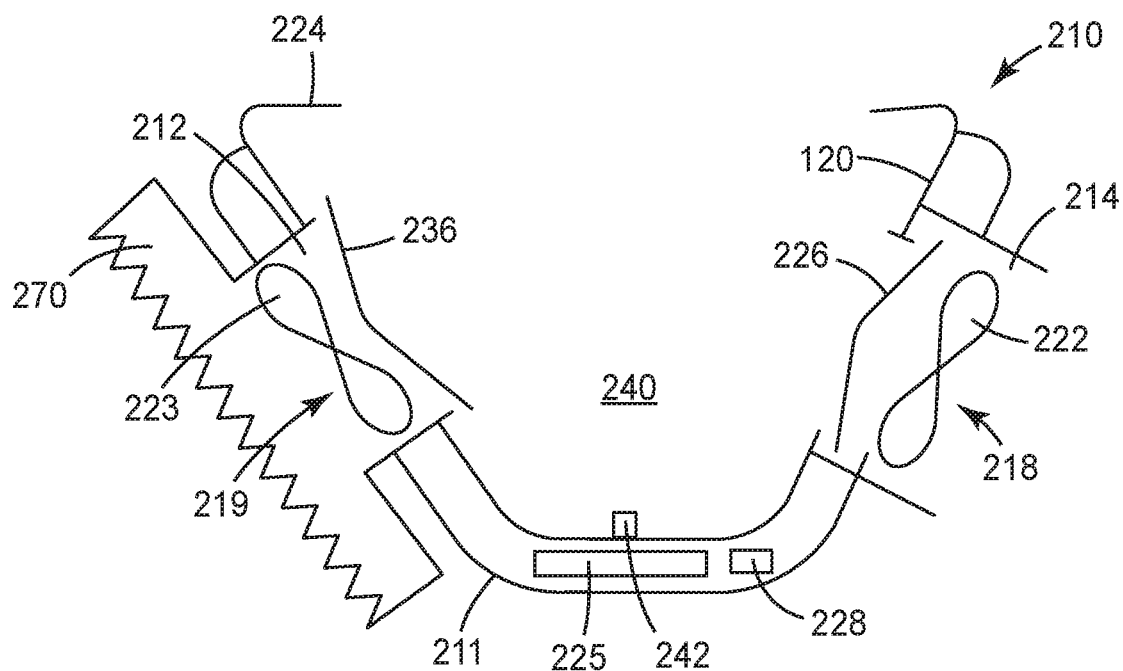
FIG. 9 is a schematic representation of the exhaust apparatus of a first embodiment of the present disclosure connected to a personal protection respiratory device.

FIG. 9 shows a first embodiment 210 of the exhaust apparatus of the present disclosure in use with a respirator 120. The apparatus 210 has a housing 211 (not shown for clarity) similar to that shown in FIGS. 1 to 7 but reconfigured to house the following features of the disclosure.

It will be appreciated that, like the apparatus 10 of FIGS. 1 to 7, the apparatus of the present disclosure is intended for use with a negative pressure respiratory mask 120 as described and defined above. That is to say, the term is used to mean any form of respirator intended to fit the face of the wearer 100 in a substantially sealed configuration causing the air inhaled and exhaled by the wearer 100 to pass through a filter body or a filter portion of the respirator or exhalation valve). Negative pressure respiratory mask 120 can be full or half facepiece mask, depending upon the hazard of concern. Again, these masks utilise a filter which prevents the inhalation of contaminants, particles, gases and vapours from the air inhaled by the wearer.

The housing defines an air duct in the form of inlet 212, an air duct in the form of outlet 214, an outlet blower 218 and an inlet blower 219. The housing 211 also houses a battery 225 and a controller 228.

A filter cartridge 270 is attached to the respirator mask 120 at inlet 212. An inhalation valve 236 is positioned within inlet 212 on the inside of the respirator mask 120. The inhalation valve 136 opens as a wearer 100 draws an inhaled breath. An exhalation valve 226 is positioned within the outlet. The exhalation valve 226 opens when a wearer 100 expels an exhaled breath. The inhalation valve 236 and exhalation valve 226 are one-way diaphragm valves.

Similar to that shown in FIGS. 1 to 7, the respiratory mask 120 has a conformable gasket or seal 224 which generally encloses the wearer's mouth and nose. The mask 220 defines a filtered air cavity 240.

The outlet blower 218 has a motor (not shown for clarity) which drives a outlet fan 222 and which is powered by the battery 225 and is in communication with, and controlled by, the controller 228. Similarly, the inlet blower 219 has a motor which drives an inlet fan 223 and which is powered by the battery 225 and is in communication with, and controlled by, the controller 228. The blowers 218, 219 collectively form a blower assembly.

The wearer's breathing cycle is detected by measuring the pressure of the filtered air volume in the filtered air cavity 240 via a pressure sensor 242 in communication with the controller 228.

Accordingly, in some embodiments, the controller 228 is able to continuously monitor the pressure in the cavity 240 and control the blowers 218, 219 via the motors in order to ensure that the inlet fan 223 is preferably only operating during the inhale breath of the wearer 100 and that the outlet fan 222 is preferably only operating during the exhale breath of the wearer 100. This reduces the inhalatory effort required in order to overcome the pressure drop across the filter as will now be described in further detail below.

Figure 10:
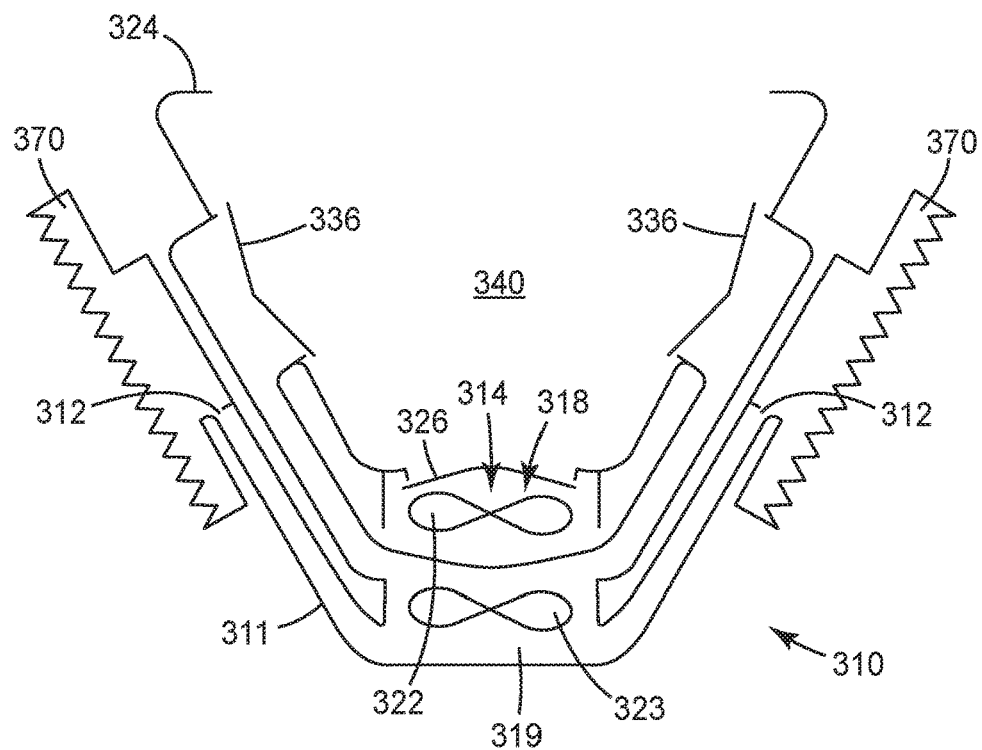
FIG. 10 is a schematic representation of the airflow through the exhaust apparatus of a second embodiment of the present disclosure connected to a personal protection respiratory device.

FIG. 10 shows a second embodiment 310 of the exhaust apparatus of the present disclosure which has two filters 370 as opposed to the single filter 170 of the first embodiment as shown in FIG. 9. The apparatus 310 has a housing 311 similar to that shown in FIGS. 1 to 7 but reconfigured to house the following features of the present disclosure. The housing defines an air duct in the form of first and second inlets 312, each of which is associated with a filter 370, an air duct in the form of outlet 314, an outlet blower 318 and an inlet blower 319. The housing 311 also houses a battery and a controller (which are not shown for clarity). The blowers 318, 319 collectively forma blower assembly.

The filter cartridges 370 are attached to the respirator mask 120 at inlets 312. Inhalation valves 336 are positioned on the inside of the respirator mask 120. The inhalation valves 336 open as a wearer 100 draws an inhaled breath. An exhalation valve 326 is positioned within the outlet 314. The exhalation valve 326 opens when a wearer 100 expels an exhaled breath. The inhalation valves 336 and exhalation valve 326 are one-way diaphragm valves.

Similar to that shown in FIGS. 1 to 7, the respiratory mask 120 has a conformable gasket or seal 324 which generally encloses the wearer's mouth and nose. The mask 320 defines a filtered air cavity 340.

The outlet blower 318 has a motor (not shown for clarity) which drives a outlet fan 322 and which is powered by the battery and is in communication with, and controlled by, the controller. Similarly, the inlet blower 319 has a motor which drives an inlet fan 323 and which is powered by the battery and is in communication with, and controlled by, the controller.

The wearer's breathing cycle is detected by measuring the pressure of the filtered air volume in the filtered air cavity 240 via a pressure sensor in communication with the controller.

Accordingly, in some embodiments, the controller is able to continuously monitor the pressure in the cavity 340 and control the blowers 318, 319 via the motors in order to ensure that the inlet fan 323 is substantially only operating during the inhale breath of the wearer 100 and that the outlet fan 322 is substantially only operating during the exhale breath of the wearer 100. This reduces the inhalatory effort required in order to overcome the pressure drop across the filter as will now be described in further detail below.

Turning now to FIGS. 14 to 19 which show a third embodiment 410 of the exhaust apparatus of the present disclosure which is for connection to the 3M™ 6800 Series respirator and has two filters 470 arranged on either side of a respirator mask 420.

The mask 420 has a see-through face mask 421 surrounded by a conformable gasket or seal 424 which generally encloses the wearer's face. The mask 420 additionally has a conformable gasket or seal 425 (see FIG. 17) which encloses the wearer's mouth and nose. The mask 420 defines a filtered air cavity 440 within the seal 425.

The apparatus 410 has an air duct in the form of first and second inlets 412, each of which is associated with a filter 470, an air duct in the form of first and second outlets 414, an outlet blower 418 and an inlet blower 419. The apparatus 410 also has a battery and a controller (which are not shown for clarity). The blowers 418, 419 collectively form a blower assembly.

Figure 18:
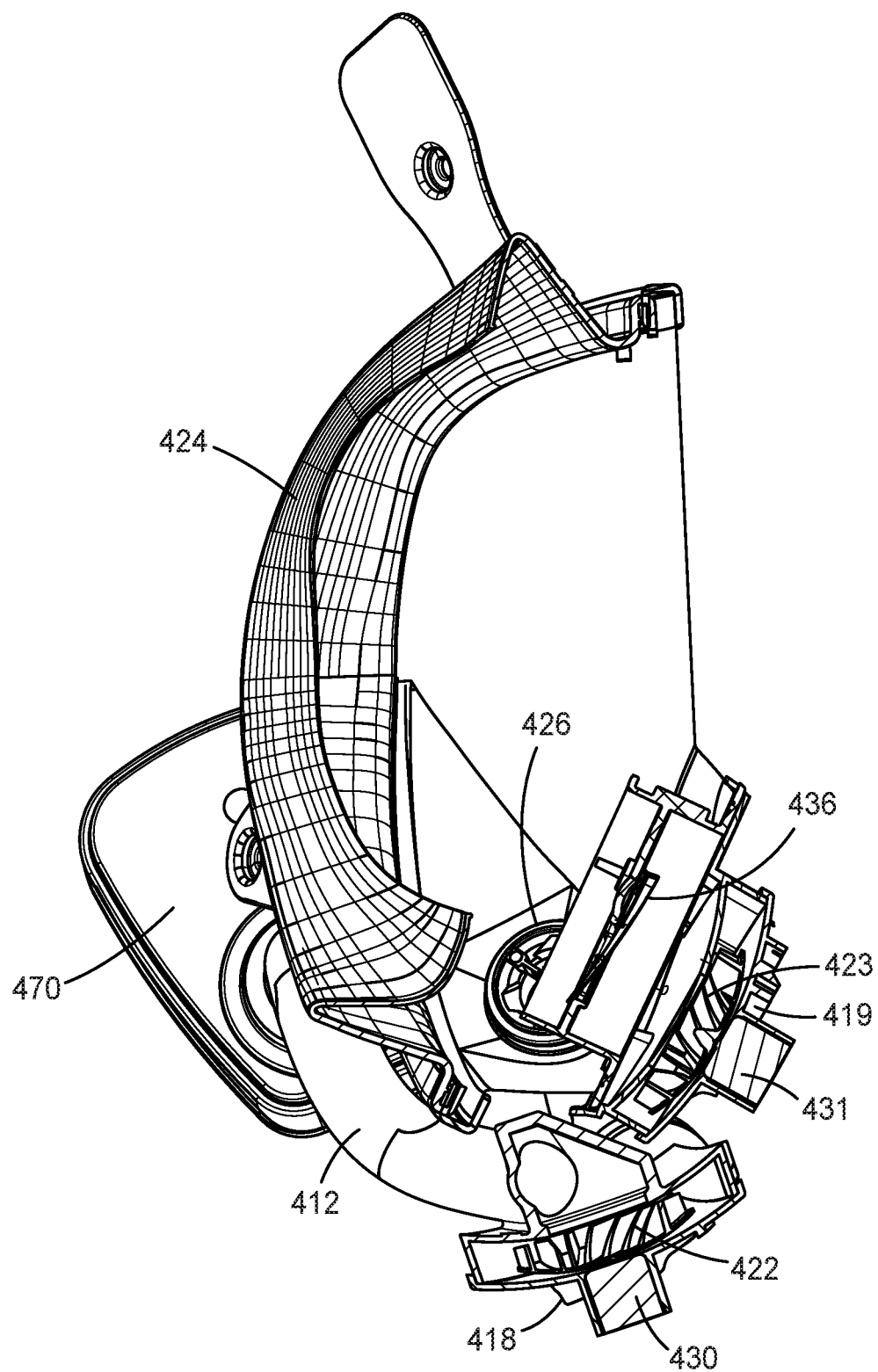
FIG. 18 is a side view of the exhaust apparatus of FIG. 14 sectioned along line XVIII-XVIII in FIG. 15.
Figure 19:
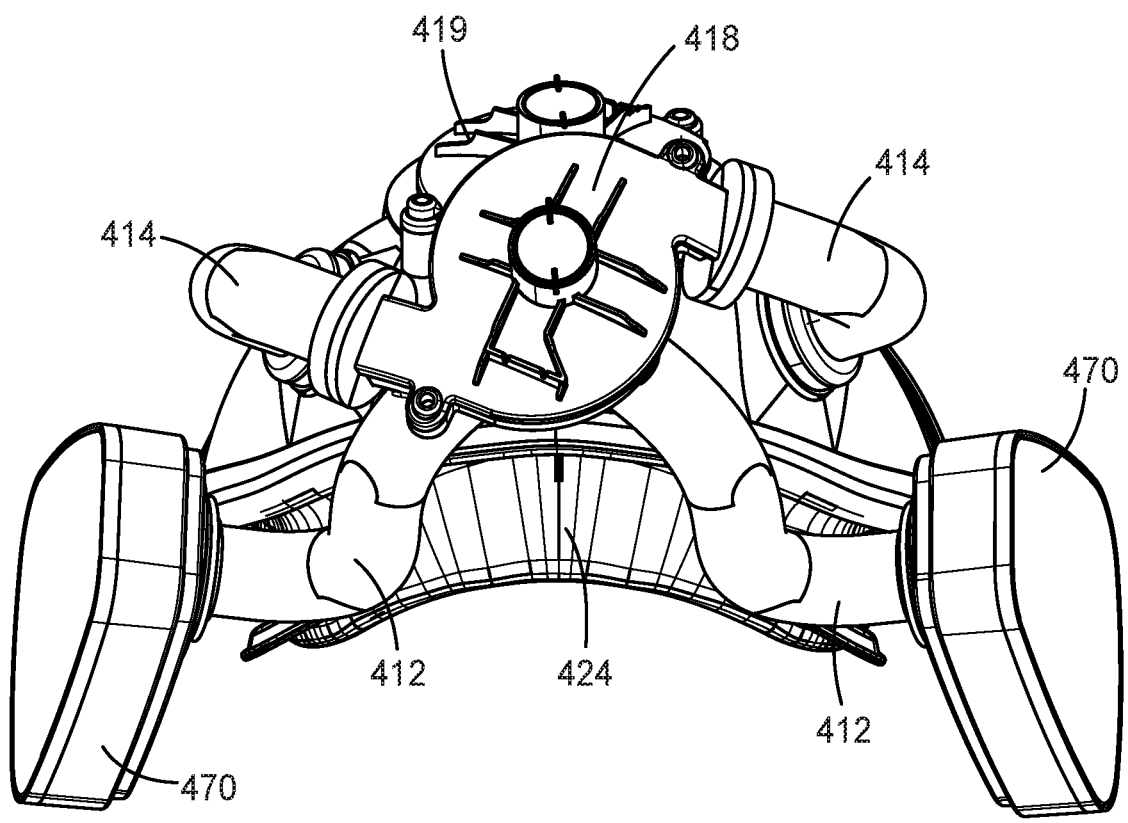
FIG. 19 is a bottom view of the exhaust apparatus of FIG. 14

The filter cartridges 470 are attached to the respirator mask 420 at inlets 412. An inhalation valve 436 (see FIG. 18) is positioned within the inlet blower 419. The inhalation valve 436 opens as a wearer 100 draws an inhaled breath. First and second exhalation valves 426 are positioned at the fluidic entrance to the first and second outlets 414 as shown in FIG. 18. The exhalation valves 426 open when a wearer 100 expels an exhaled breath. The inhalation valve 436 and exhalation valves 426 are one-way diaphragm valves.

The outlet blower 418 has a motor 430 which drives an outlet fan 422 (see FIG. 18) and which is powered by the battery and is in communication with, and controlled by, the controller. Similarly, the inlet blower 419 has a motor 431 which drives an inlet fan 323 (again, see FIG. 18) and which is powered by the battery and is in communication with, and controlled by, the controller.

The wearer's breathing cycle is detected by measuring the pressure of the filtered air volume in the filtered air cavity 440 via a pressure sensor in communication with the controller.

Accordingly, in some embodiments, the controller is able to continuously monitor the pressure in the cavity 440 and control the blowers 418, 419 via the motors in order to ensure that the inlet fan 423 is substantially only operating during the inhale breath of the wearer 100 and that the outlet fan 422 is substantially only operating during the exhale breath of the wearer 100. This reduces the inhalatory effort required in order to overcome the pressure drop across the filter as will now be described in further detail below.

Figure 11:
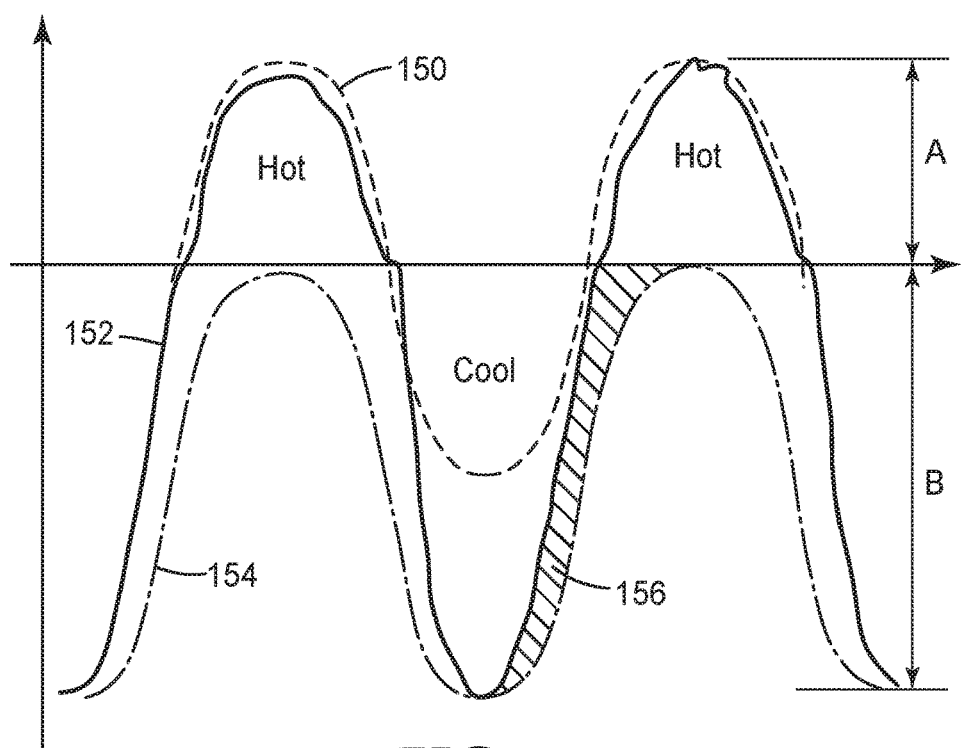
FIG. 11 is a chart illustrating the pressure and flow characteristics of the prior art device of WO2014/081788.
Figure 16:
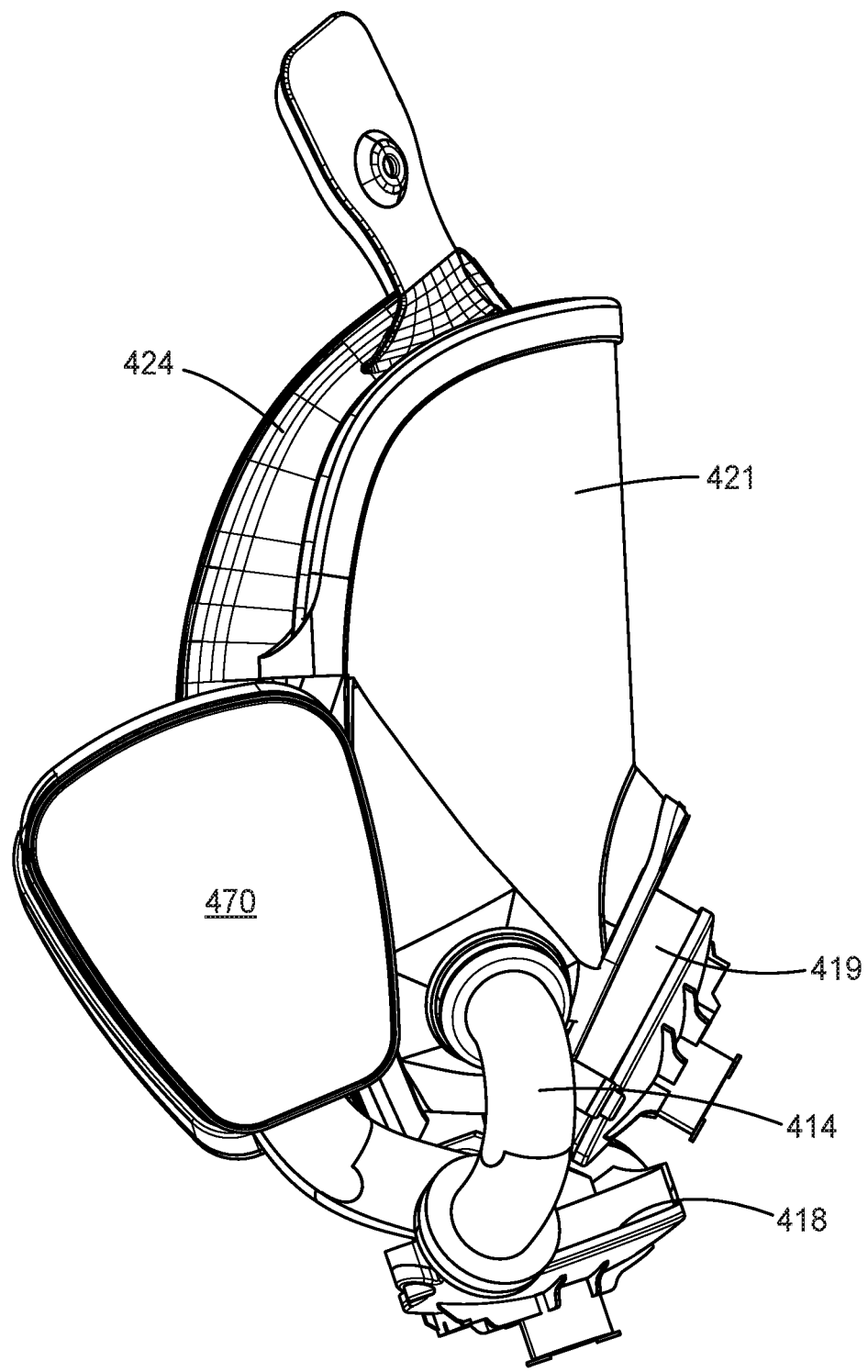
FIG. 16 is a side view of the exhaust apparatus of FIG. 14.
Figure 17:
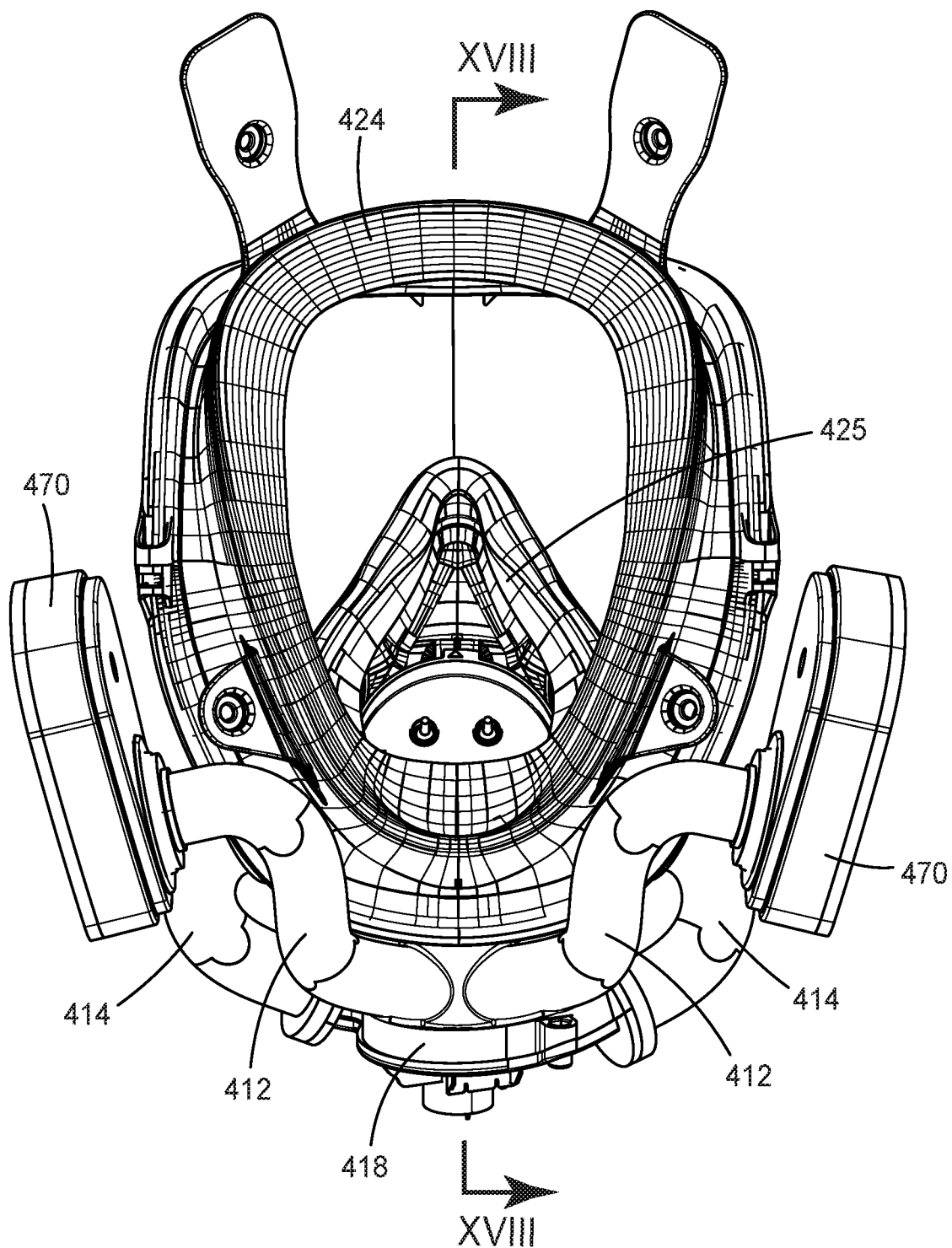
FIG. 17 is a rear view of the exhaust apparatus of FIG. 14.

Referring to FIG. 16, it will be noted that the filters 470 are positioned substantially rearwardly of the face mask 421. This presents the advantage to the user of minimizing the extent to which the filters impair the field of vision. FIG. 11 shows a representation of pressure in, and flow rate through, the filtered air cavity in the prior art device of WO2014/081788. The dashed line 150 represents the flow rate through the mask and the solid line 152 represents the pressure in the mask cavity when the device is switched off. The flow rate naturally oscillates about zero as the wearer breaths in cool air through inhale breath B and breaths out hot air through exhale breath A. With the device switched on, the flow rate remains unchanged as the wearer continues to breathe the volume of air required to match respiratory demand. However, the pressure line drops to the extended dashed line 154 as the fan operates to maintain a negative pressure in the mask throughout both the inhale and exhale breath. This can preferably only be achieved by pulling additional air through the filters during the inhale stroke. This additional volume of air is driven by the additional negative pressure shown in the hatched area 156. The additional flow volume through the filter limits filter life. Furthermore, the additional negative pressure must be overcome by additional respiratory effort if the same flow rate is to be maintained. This additional respiratory effort may itself cause increased respiratory load resulting in an increased breathing rate.

Figure 12:
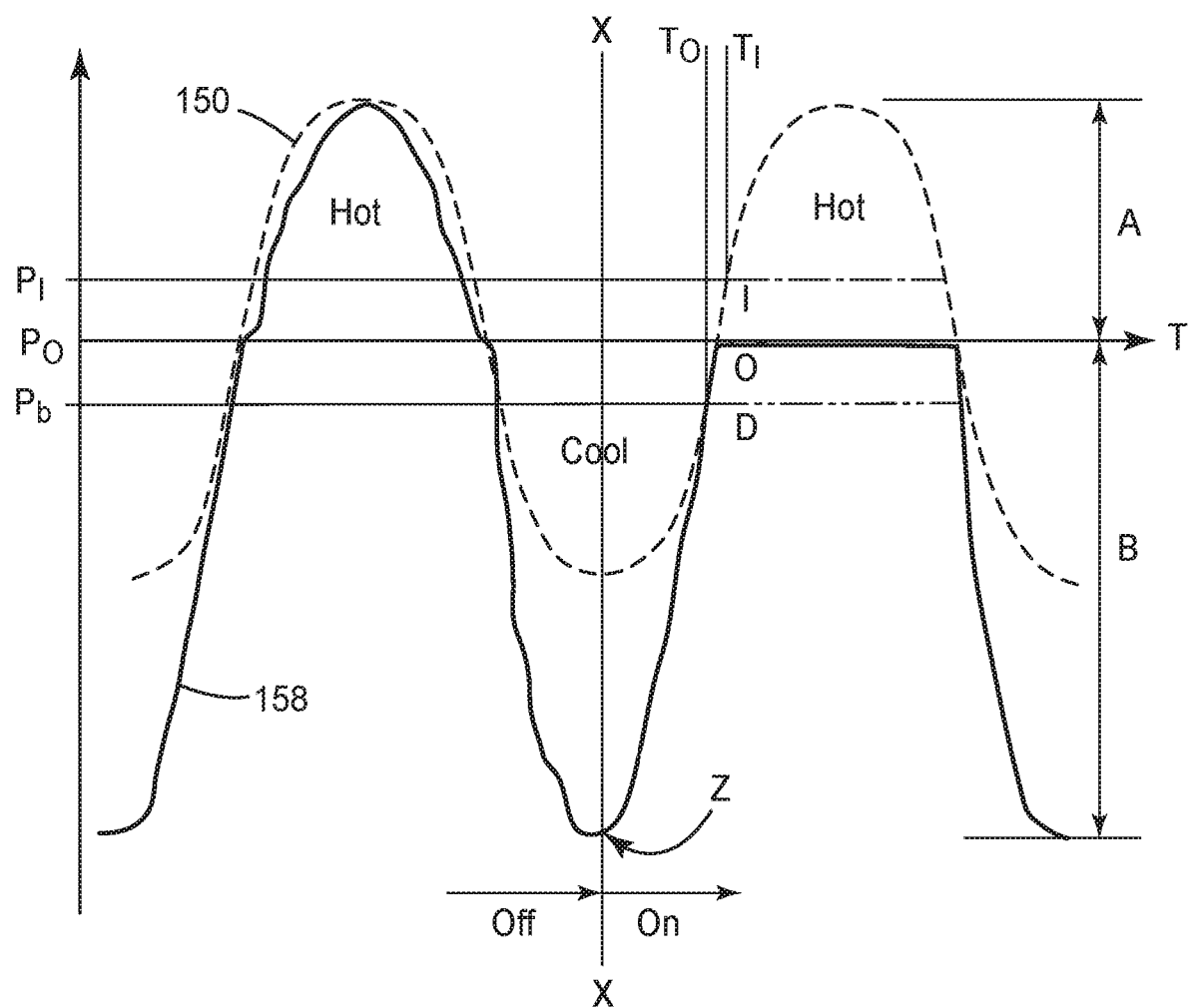
FIG. 12 is a chart illustrating the pressure and flow characteristics of the exhaust apparatus of FIGS. 1 to 7.

Turning now to FIG. 12, the chart shows a representation of pressure in, and flow rate through, the filtered air cavity of the known exhaust apparatus 10 as described in FIGS. 1 to 7. The dashed line 150 once again represents the flow rate through the mask 100 and the solid line 158 represents the pressure in the mask cavity 140. To the left of the centerline X-X the exhaust apparatus 10 is switched off and to the right it is switched on. With the exhaust apparatus 10 switched off the pressure oscillates about zero subject to the larger maximal negative pressure resulting from the pressure drop across the filters. With the device switched on, the pressure line rises from its low point Z towards zero as the wearer inhales through the filters. As the wearer breaths in through the filter, the controller 28 monitors the rise in pressure in the cavity 140 via the pressure conduit 34. When the controller detects a predetermined pressure in the cavity 140, in this instance $P_0$ (equal to zero), the controller 28 controls the motor 20 to initiate the blower 12. This pulls air from the cavity 140 in order to assist the breathing of the wearer. The blower 12 continues to operate until such time as the pressure in the cavity 140 falls below the predetermined $P_0$ at which point the controller stops the motor 20.

The extent of exhale breath assist may be varied by decreasing the predetermined pressure, as indicated by $P_D$, or increasing the predetermined pressure, as indicated by $P_I$. $P_D$ delivers a cooler feel to the wearer and $P_I$ a warmer feel. It is conceivable that this variation in cooling effect could be controlled by the wearer in response to the operating conditions.

However, it will be noted that the magnitude of the inhalatory pressure in the mask cavity 140 as represented by line 158, which peaks at point Z, remains considerable as the device of FIGS. 1 to 7 preferably does not provide any assistance to the user during the inhalation breath.

Figure 13:
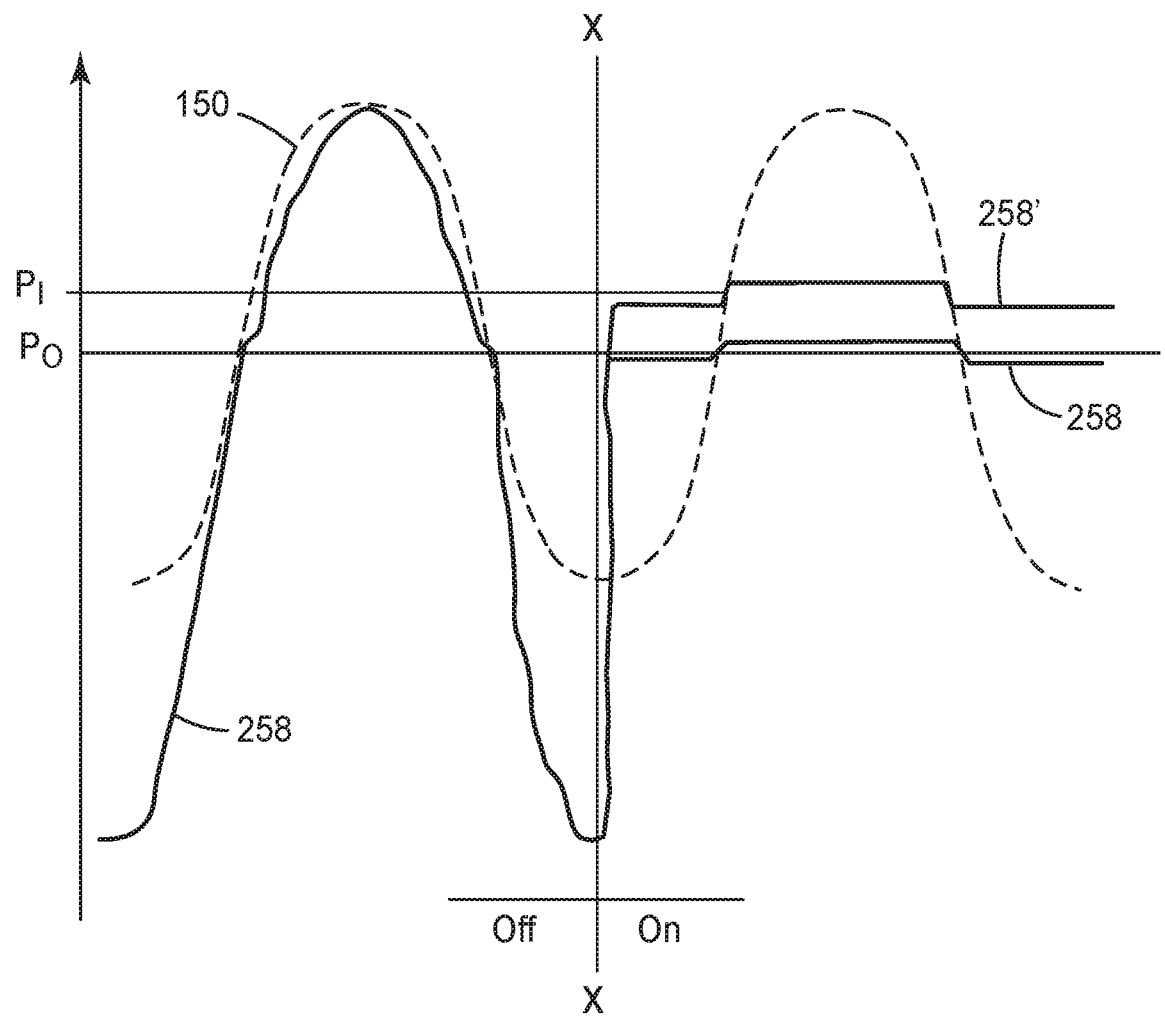
FIG. 13 is a chart illustrating the pressure and flow characteristics of the exhaust apparatus of the present disclosure.
Figure 14:
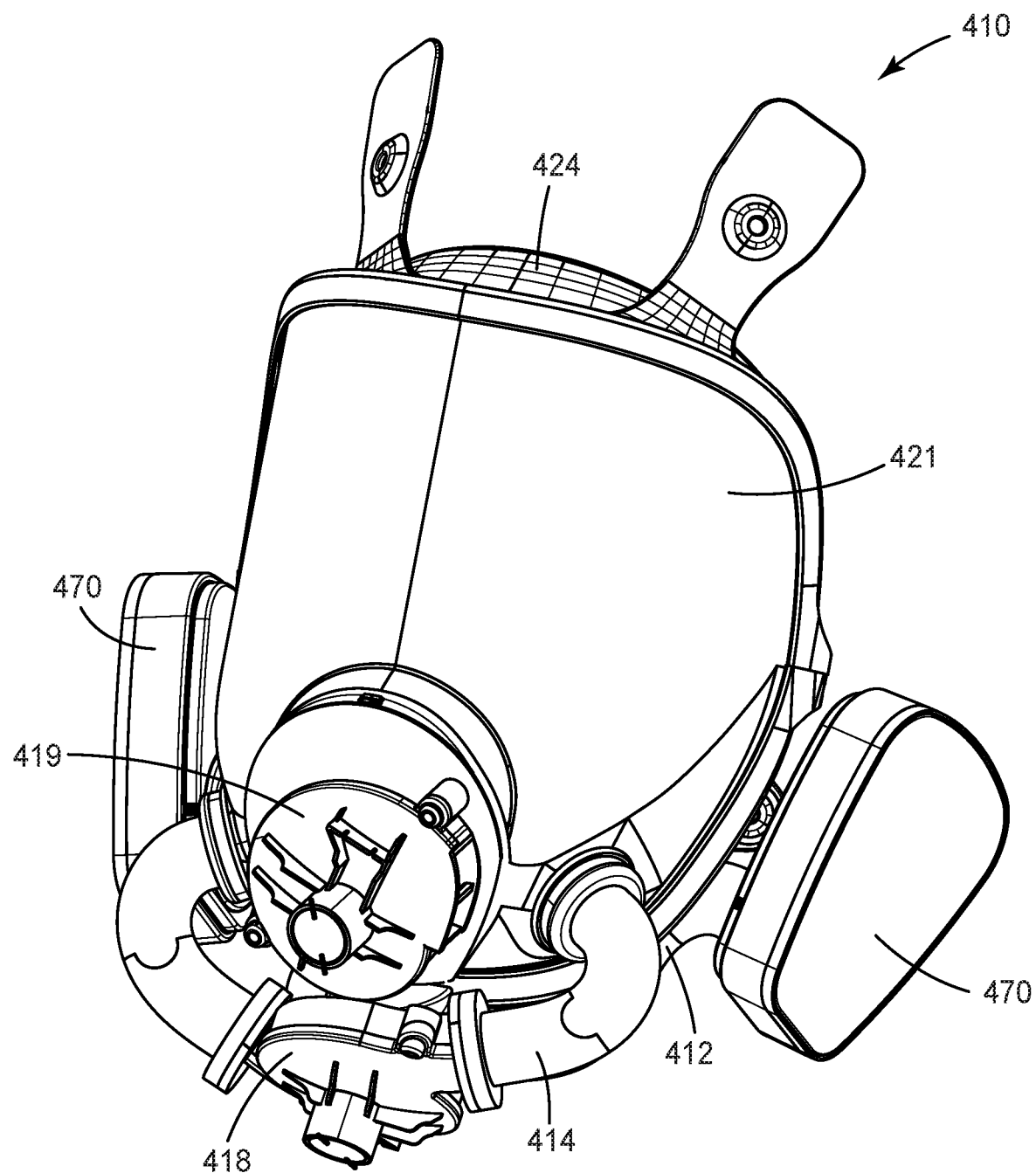
FIG. 14 is an isometric view an exhaust apparatus of a third embodiment of the present disclosure.
Figure 15:
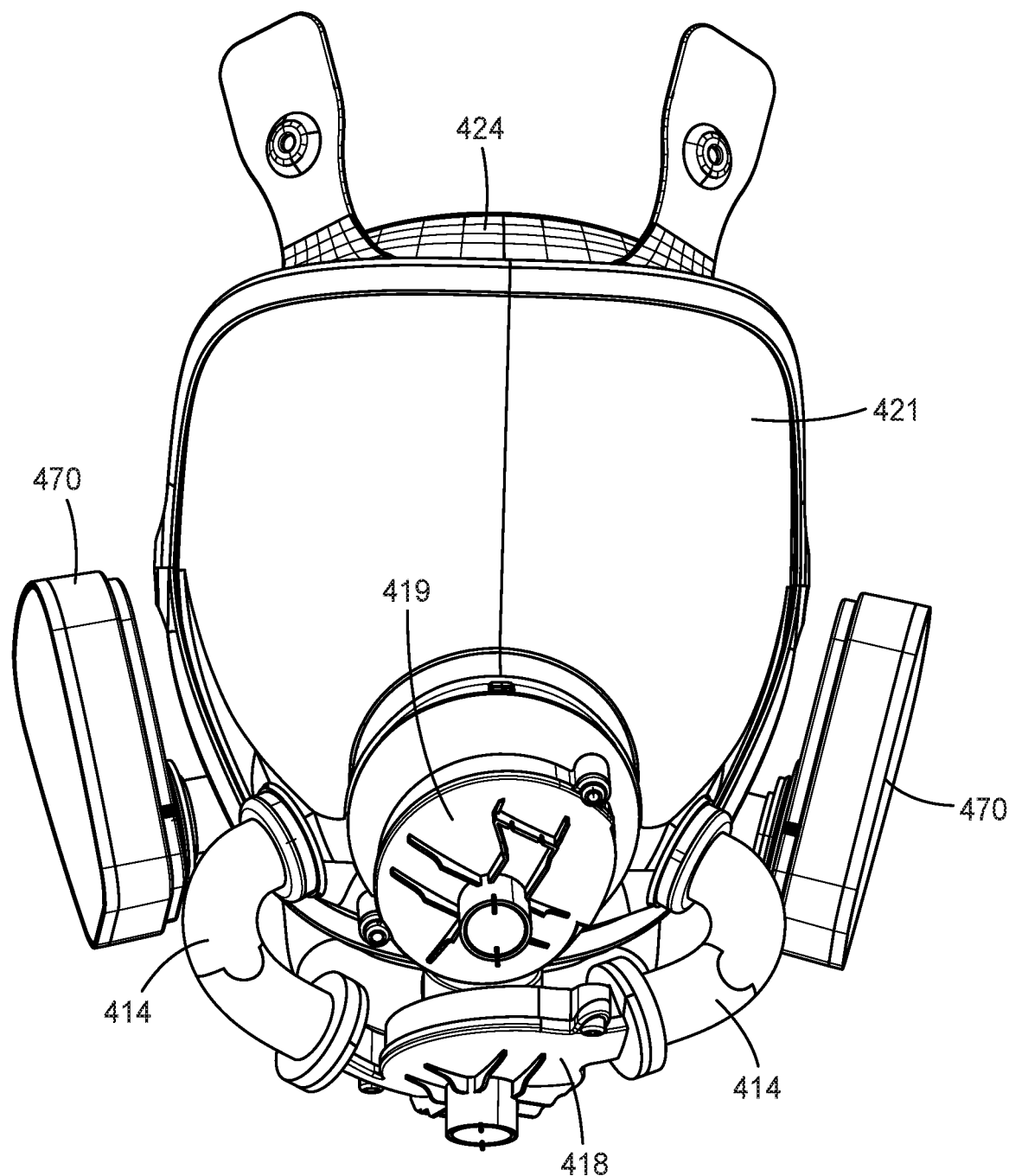
FIG. 15 is a front view of the exhaust apparatus of FIG. 14.

Turning now to FIG. 13 in which the chart shows a representation of pressure in, and flow rate through, the filtered air cavity of the first, second and third embodiments of exhaust apparatus of the present disclosure. The dashed line 150 once again represents the flow rate through the mask 100. The solid line 258 represents the pressure in the mask cavity 240, 340, 440. To the left of the centerline X-X the exhaust apparatus 210, 310, 410 is switched off and to the right it is switched on. With the exhaust apparatus 210, 310, 410 switched off the pressure oscillates about zero subject to the larger maximal negative pressure resulting from the pressure drop across the filters. With the device switched on, the controller detects a negative pressure in the cavity 240, 340, 440 the controller controls the motor to initiate the blower 219, 319, 419. This pulls air through the filters 270, 370, 470 into the cavity 240, 340, 440 in order to assist the inhalation breath of the wearer. As a result the rise in pressure in the cavity 240, 340 increases rapidly as indicated by the pressure line 159 rising rapidly from its low point Z towards zero as the wearer inhales through the filters 270, 370, 470. As the wearer breaths in through the filter, the controller 28 monitors the rise in pressure in the cavity 240, 340, 440. When the controller detects a predetermined pressure in the cavity 240, 340, 440 in this instance $P_0$ (equal to zero), the controller cuts power to the blower 219, 319, 419 and initiates the blower 218, 318, 418. This pulls air from the cavity 140 in order to assist the exhale breath of the wearer. The blower 218, 318, 418 continues to operate until such time as the pressure in the cavity 140 falls below the predetermined $P_0$ at which point the controller switches power back to the blower 219, 319, 419.

In this manner the pressure in the cavity is maintained as close to zero pressure as possible in order to provide the user with a natural feeling of breathing in and out without the heat build-up associated with an unassisted exhale breath and without the need to overcome the pressure drop across the filter during the inhale breath. This significantly increases the comfort and safety experienced by the user.

It is conceivable within the scope of the disclosure that the controller could control the blowers 218, 318, 418, 219, 319, 419 in the manner described above in order to achieve an average pressure greater than atmospheric. Line 258' in FIG. 13 represents such a situation where the predetermined pressure at which the controller switches power to the blowers 218, 318, 418, 219, 319, 419 in increased to $P_1$. This provides the advantage of maintaining a positive pressure within the cavity 240, 340, 440 which serves to minimize the risk of unfiltered air passing into the cavity between the mask and the face of the wearer.

It will be appreciated that whilst FIG. 13 depicts the same predetermined pressure at the beginning and the end of the exhalation breath, that is to say $P_0$, for example, remains constant throughout the exhalation breath, it is conceivable within the scope of the disclosure that the blowers 218, 318, 418, 219, 319, 419 could be started at a first predetermined pressure and stopped at a second predetermined pressure. Equally it is conceivable within the scope of the disclosure that the blowers 218, 318, 418, 219, 319, 419 could run consecutively for a short period of time in order to account for hysteresis in the system.

The invention claimed is:

1. An exhaust apparatus for connection to a personal protection respiratory device that defines a filtered air volume adjacent to the face of a wearer and comprises at least one exhalation valve and at least one inhalation valve, the apparatus comprising:
    a housing adapted to be connected to the personal protection respiratory device;
    a first air duct defined by the housing and in fluid connection with the at least one exhalation valve,
    a second air duct defined by the housing and in fluid connection with the at least one inhalation valve,
    a blower assembly disposed within the housing for selectively directing air through the first and second ducts,
    the blower assembly being responsive to the wearer's respiratory cycle so that, in use, the blower draws a substantial portion of the wearer's exhaled breath through the first duct and out through the at least one exhalation valve,
    the blower draws a substantial portion of the wearer's inhaled breath through the second duct and in through the at least one inhalation valve, and
    wherein the housing comprises an upwardly extending section and a rearwardly extending section, wherein the upwardly extending section houses the first air duct, the second air duct, and the blower assembly, and further wherein the rearwardly extending section houses the battery.

2. The exhaust apparatus as claimed in claim 1, the blower assembly comprising
    a first blower associated with the first air duct, and
    a second blower associated with the second air duct,
    the first and second blowers being responsive to the wearer's respiratory cycle, wherein
    the first blower operates throughout the wearer's exhale breath, or a substantial period thereof, and does not operate throughout the wearer's inhale breath, or a substantial period thereof, and
    the second blower operates throughout the wearer's inhale breath, or a substantial period thereof, and does not operate throughout the wearer's exhale breath, or a substantial period thereof.

3. The exhaust apparatus as claimed in claim 2, further comprising:
    a controller,
    a sensor for sensing a parameter generated by the wearer's breathing cycle and sending a signal indicative of the parameter to the controller,
    the controller being in communication with the sensor and the first and second blower,
    wherein the controller operates the first and second blower in response to the signal.

4. The exhaust apparatus as claimed in claim 3 wherein the parameter is pressure, the sensor is a pressure sensor and the signal is a pressure signal.

5. The exhaust apparatus as claimed in claim 4 wherein the pressure is sensed in a filtered air volume of the personal protection respiratory device.

6. The exhaust apparatus as claimed in claim 4 wherein the pressure is sensed downstream of the exhalation valve or upstream of the inhalation valve.

7. The exhaust apparatus as claimed in claim 1 wherein the controller starts the first blower and stops the second blower when the pressure sensed by the pressure sensor reaches a first predetermined pressure or the rate of change of pressure reaches a first predetermined rate.

8. The exhaust apparatus as claimed in claim 7 wherein the controller stops the first blower and starts the second blower when the pressure sensed by the pressure sensor falls below a second predetermined pressure or the rate of change of pressure reaches a second predetermined rate.

9. The exhaust apparatus as claimed in claim 8 wherein the first predetermined pressure and the second predetermined pressure are a common predetermined pressure.

10. The exhaust apparatus as claimed in claim 9 wherein the common predetermined pressure is substantially ambient pressure so that the controller starts the first blower and stops the second blower substantially at the initiation of the wearer's exhale breath and stops the first blower and starts the second blower substantially at the end of the wearer's exhale breath.

11. The exhaust apparatus as claimed in claim 9 wherein the common predetermined pressure is higher than ambient pressure so that the controller starts the first blower and stops the second blower momentarily after the initiation of the wearer's exhale breath and stops the first blower and starts the second blower momentarily before the end of the wearer's exhale breath.

12. The exhaust apparatus as claimed in claim 9 wherein the common predetermined pressure is lower than ambient pressure so that the controller starts the first blower and stops the second blower momentarily before the initiation of the wearer's exhale breath and stops the first blower and starts the second blower momentarily after the end of the wearer's exhale breath.

13. The exhaust apparatus as claimed in claim 8 wherein the first predetermined pressure is greater than the second predetermined pressure so that the controller starts the first blower and stops the second blower momentarily after the initiation of the wearer's exhale breath and stops the first blower and starts the second blower momentarily after the end of the wearer's exhale breath.

14. The exhaust apparatus as claimed in claim 8 wherein the second predetermined pressure is greater than the first predetermined pressure so that the controller starts the first blower and stops the second blower momentarily before the initiation of the wearer's exhale breath and stops the first blower and starts the second blower momentarily before the end of the wearer's exhale breath.

15. The exhaust apparatus as claimed in claim 2, wherein the first and second blowers further comprise an inlet, a motor, a fan, and an outlet.

16. The exhaust apparatus as claimed in claim 1, wherein the personal protection respiratory device is disposable or reusable and filters particulate, gas or vapour and is selected from a group consisting of half mask, full face, and tight-fitting hood respirators.

17. The exhaust apparatus as claimed in claim 1, further comprising a battery disposed in the housing and electrically connected to the blower assembly.

18. The exhaust apparatus as claimed in claim 3, wherein the controller is disposed within the housing.

19. The exhaust apparatus as claimed in claim 18, wherein the rearwardly extending section houses the controller.

* * * * *